United States Patent
Niven et al.

(10) Patent No.: US 6,830,334 B2
(45) Date of Patent: Dec. 14, 2004

(54) ANTERIOR CHAMBER DIAMETER MEASUREMENT SYSTEM FROM LIMBAL RING MEASUREMENT

(75) Inventors: Gregg D. Niven, Kaysville, UT (US); Timothy N. Turner, West Jordan, UT (US)

(73) Assignee: Bausch & Lomb Incorporated, Rochester, NY (US)

( * ) Notice: Subject to any disclaimer, the term of this patent is extended or adjusted under 35 U.S.C. 154(b) by 31 days.

(21) Appl. No.: 09/918,678

(22) Filed: Jul. 30, 2001

(65) Prior Publication Data

US 2003/0020871 A1 Jan. 30, 2003

(51) Int. Cl.[7] ............................. A61B 3/14; A61B 3/10
(52) U.S. Cl. ....................... 351/206; 351/221; 356/635
(58) Field of Search .................. 351/200, 205, 351/206, 208–214, 221, 246; 356/3–3.16, 4.01, 4.03, 51, 625, 635; 382/106, 190, 199, 203

(56) References Cited

U.S. PATENT DOCUMENTS

| 4,113,389 | A | * | 9/1978 | Kaye | 356/623 |
|---|---|---|---|---|---|
| 4,465,374 | A | * | 8/1984 | Pryor et al. | 356/635 |
| 4,761,071 | A | * | 8/1988 | Baron | 351/212 |
| 5,094,521 | A | * | 3/1992 | Jolson et al. | 351/210 |
| 5,576,832 | A | * | 11/1996 | Yamamoto | 356/625 |
| 5,865,832 | A | * | 2/1999 | Knopp et al. | 351/209 |
| 5,877,849 | A | * | 3/1999 | Ramer et al. | 356/3.01 |
| 6,110,110 | A | * | 8/2000 | Dublin et al. | 600/405 |
| 6,116,738 | A | * | 9/2000 | Rorabaugh | 351/247 |
| 6,193,371 | B1 | * | 2/2001 | Snook | 351/212 |
| 6,299,307 | B1 | * | 10/2001 | Oltean et al. | 351/210 |
| 6,587,183 | B1 | * | 7/2003 | Uomori et al. | 356/3.1 |

OTHER PUBLICATIONS

Grimmett et al., Measurement of Radial Keratotomy Clear Zone Diameters, J Refract Surg 1998, vol. 14, pp. 331–337.*

* cited by examiner

Primary Examiner—Brian L. Casler
Assistant Examiner—John R Sanders
(74) Attorney, Agent, or Firm—Michael L. Smith

(57) ABSTRACT

A system (10) for measuring a diameter of a limbus of an eye (12). An image recorder (14) is at a known location apart from the eye and records an illuminated limbus image. An illumination source (16) at a known location relative to the image recorder (14) illuminates the limbus. A computer device (18) connected to the image recorder (14) determines the diameter of the limbus from the recorded illuminated limbus image.

23 Claims, 3 Drawing Sheets

ANTERIOR CHAMBER DIAMETER MEASUREMENT SYSTEM FROM LIMBAL RING MEASUREMENT

BACKGROUND OF THE INVENTION

I. Field of the Invention

The present invention relates to a system for measuring the limbus-to-limbus diameter of an eye and more specifically, to a system using laser-slit illumination of the eye for measurement of the limbal diameter and deriving an anterior chamber diameter from the limbal diameter.

II. Description of the Related Art

A common measurement for an eye care professional in fitting lenses or performing surgical procedures such as laser assisted in-situ keratomileusis (LASIK) or for inserting an inter-corneal lens (ICL) is to measure the diameter of the cornea or the limbus-to-limbus measurement. The limbus is a junction of the cornea of the eye and the sclera which extends all around the periphery of the cornea. This limbal diameter measurement is used to determine the diameter of the external boundary of the cornea and is used with LASIK surgery or contact lens fitting. This limbal diameter measurement is also used to determine the internal interior chamber diameter or angle-to-angle measurement which is critical for properly fitting an ICL in a patient's eye.

It is known to obtain the limbal diameter measurement using what is commonly known as a Holliday disk, or a scale held near the patient's eye, or a caliper held near the patient's eye. None of these known techniques provide for a precise measurement of the limbal diameter.

If the calculated limbal diameter is sufficiently larger than the actual limbal diameter, it is possible that an ICL that is too large may be incorrectly inserted into the patient's eye; thereby causing pressure to the trabecular meshwork and Schlemm's canal. These problems could have an adverse effect on the natural aqueous flow from the eye or on the refractive outcome following ICL implantation. Conversely, a calculated limbal diameter that is too small could result in a lens that is too small for the patient's eye. This could be problematic because the ICL could move out of place.

Therefore it is important that an easy and accurate system to measure limbal diameter be obtained.

DETAILED DESCRIPTION OF THE PREFERRED EMBODIMENTS

A system for measuring a diameter of a limbus of an eye and for determining iris-angle diameters is described below.

When a beam of light is directed on or near the annular limbal region connecting the cornea to the sclera in addition to local scatter, a continuous ring of light emanating from the limbus can be seen. This so called limbal-ring appears for both visible and infrared illumination and for both monochromatic (e.g., laser or LED) and continuous spectra (e.g., white-light slit-beam). The illuminated limbal-ring usually occurs must clearly when the illumination directly impinges the limbal region. The limbal-ring can also be seen, but with far less clarity, by indirectly illuminating the limbus via iris scatter or corneal fiber optic conduction.

It is believed that when light impinges any part of the limbus, the light enters a circumferential ring of stromal collagen fibers. These collagen fibers act as a light-pipe and operate to direct the impinging light around the entire circumference of the limbal region. The annular emanation of light thus marks an anatomical ring of collagen fibers. These collagen fibers are directly associated with the limbus and iris angle. This limbal-fiber-ring, buried within the fibrous tunic of the eye, was previously discovered with x-ray diffraction. This limbal-fiber-ring acts to maintain the shape of the internally pressurized eye at the limbal joint connecting the cornea to the sclera.

To accurately determine the diameter of the limbal-ring, the ring should preferably be clearly illuminated using the above-described light-piping effect. It is preferred that extraneous surface scatter and indirect illumination via the cornea, iris, or anterior chamber be minimized. Therefore, limbal-ring illumination is preferably accomplished using a narrow beam directly impinging the limbus.

Figure 1:
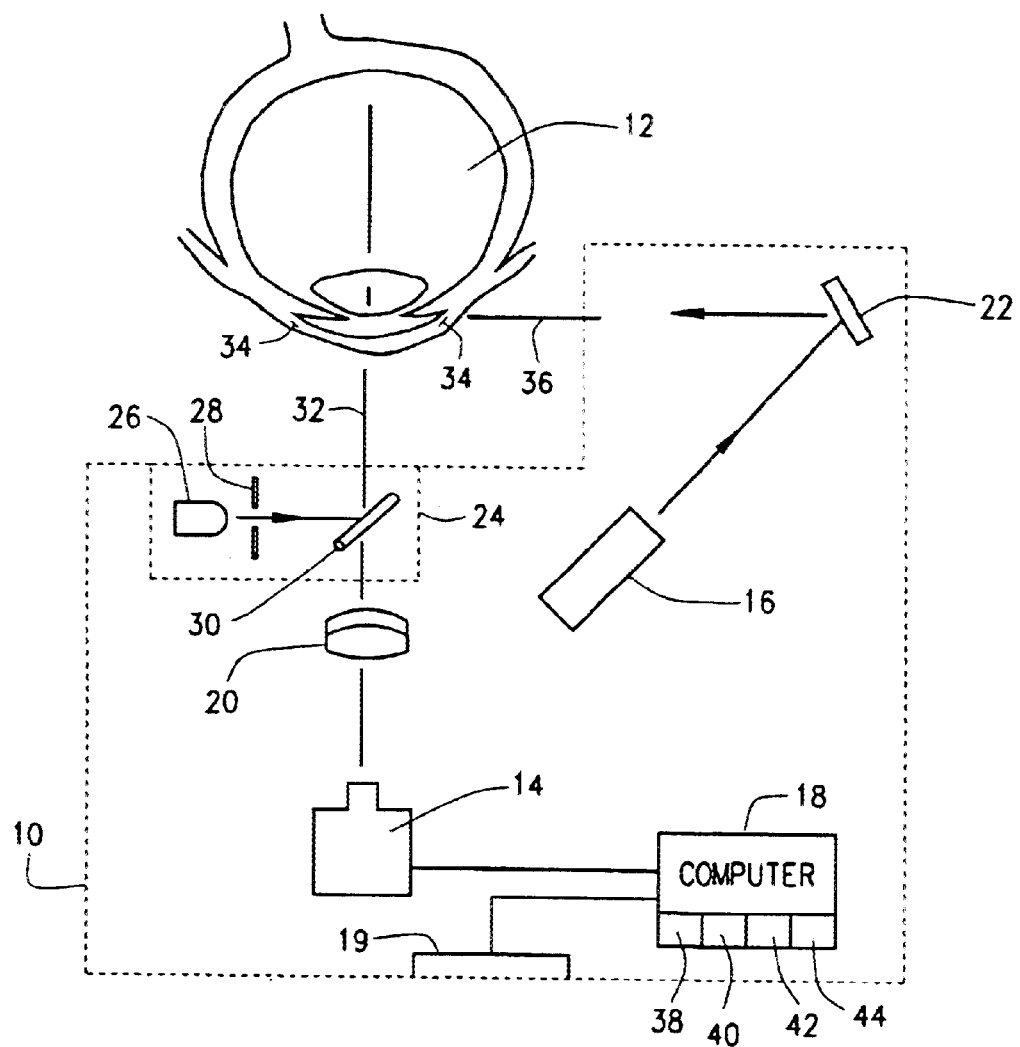
FIG. 1 is a block diagram of a system in accordance with the present invention being used on a patient's eye.

FIG. 1 shows a system 10, in accordance with the present invention, for measuring a diameter of a limbus of an eye 12. System 10 includes an image recorder 14 to be placed at a known location apart from the eye 12 for recording an illuminated limbus image, at least a first illumination source 16, and a computing device 18. An output device 19; focusing lens 20, a reflecting mirror 22, and an optional fixation target 24 are also preferably included in system 10. It will be appreciated that system 10 could be incorporated into a comprehensive eye measurement system, such as the ORBSCAN™ system sold by Bausch & Lomb or system 10 can be a hand-held stand alone system as shown in FIG. 1.

The optional fixation target 24 includes a fixation light source 26, a pin hole aperture 28, and a beam splitter 30 all cooperating to illuminate a small dot of light along line 32 so as to facilitate fixation of the eye 12 along line 32, which corresponds to the viewing axis of camera 14.

In operation illumination source 16 directs a light beam at a first known location relative to the image recorder 14 for illuminating the limbus 34 along line 36. Line 36 represents the light from illumination source 16 that has been reflected by a mirror 22. The illuminated limbal ring 34 then is recorded by image recorder 14 which is preferably a charge couple device (CCD) video camera. Computer 18, using image analysis locates the illuminated limbal position in 3-dimensional space by triangulating the beam in the surface scattered light recorded by the camera 14. The limbal diameter is then calculated from the image of the illuminated ring based on the known distance to the eye. Accurate limbal diameters cannot be determined in the region of the directly impinging light because the directly impinging light from source 16 overwhelms the camera 14 at the region of the eye immediately adjacent of the impinging light. Therefore, the limbal diameters are preferably pieced together from at least two different images. As one skilled in the art will appreciate, the registration of the different images by computer 18 is facilitated using known techniques such as iris texture and pupil edge cues.

Illumination source 16 may provide visible or infrared illumination or the preferred red laser light may be used. The preferred embodiment of illumination source 16 uses an infrared diode laser light collimated into narrow cylindrical beam or short-slit. This provides an economical unobtrusive illumination source and gives superior contrast to the iris and pupil images. As those skilled in the art will appreciate, any illumination source 16 may be used that provides adequate illumination of the limbal region in order for the camera 14 and computer 18 to record and detect the limbal region.

The image recorder, preferably a video camera such as a CCD camera 14 is focused on the limbal plane defined by line 32 and has a narrow beam of light at a fixed angle from the camera that illuminates the limbus at multiple locations. The fixed angle of the illumination source 16 from the image recorder 14 is preferably from about 25° to about 90°. The multiple illuminations are preferably implemented in sequence and can be achieved in a number of ways. A first method is where the system 10 has a single fixed beam (represented by line 36), as shown in FIG. 1, and the single fixed beam is manually repositioned a number of times (at least two) in order for the camera 14 to obtain a sufficient number of images to define the limbal diameter. A second embodiment includes two or more fixed beams, such as shown and described below in connection with FIG. 3, taking images in rapid succession. A third embodiment is where a single illumination source is constructed such that the beam impinging upon the patient's eye is rotated and scanned around the limbus and images are recorded by the camera 14 during this scanning procedure.

As those skilled in the art will appreciate, computer 18 may be a stand alone computer, such as a personal computer or it could be built into a unified instrument as is preferred and shown in FIG. 1. Computer 18 preferably includes a frame grabber 38 or other device for digitizing images from camera 14. Computer 18 preferably further includes an iris-angle calculator 42 and an ICL calculator 44 described move fully below.

After a sufficient number of illuminated limbal images are recorded by camera 14 and digitized in a memory 40 of computer 18, the computer then processes the images, as described in relation to FIG. 2 below.

Figure 2:
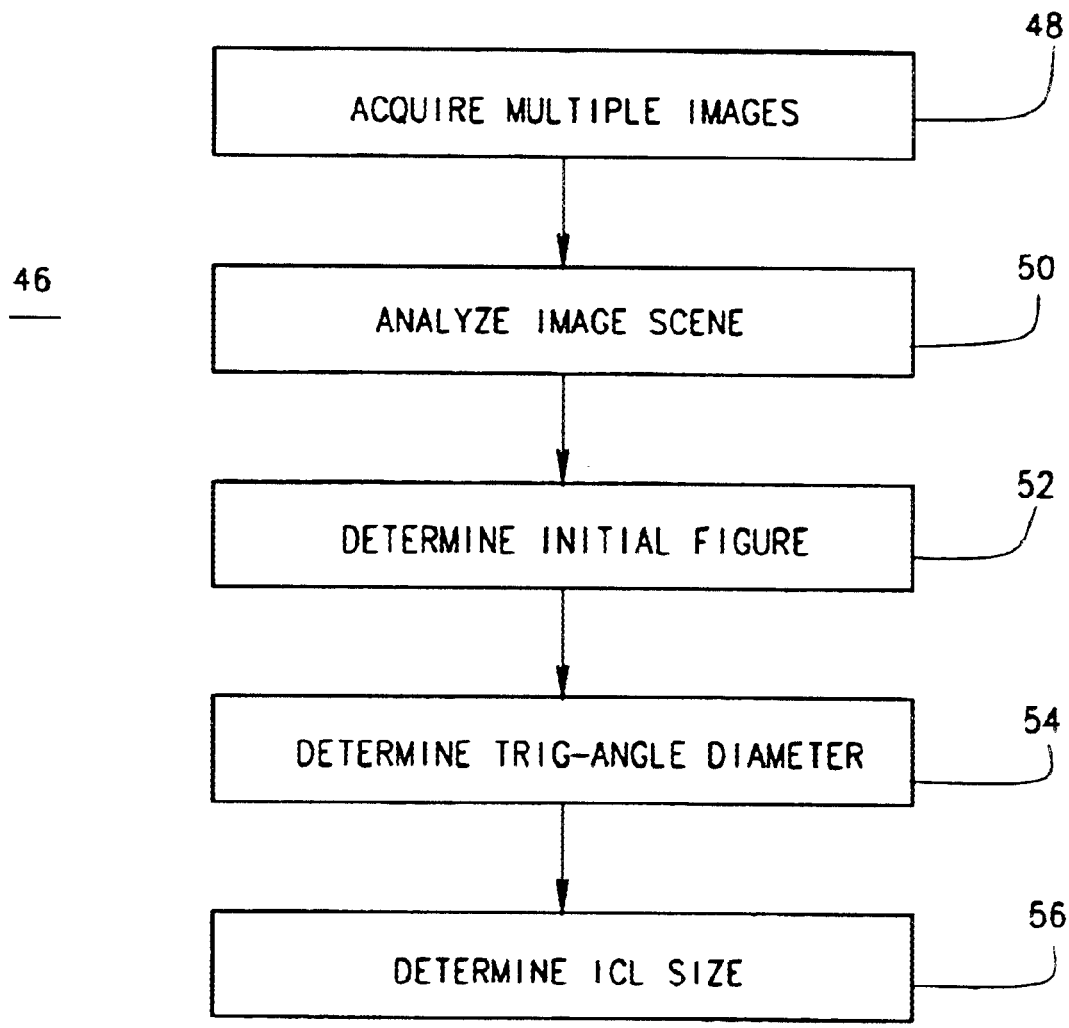
FIG. 2 is a flow diagram of a portion of the preferred system in accordance with the present invention.

FIG. 2 discloses a flow chart 46 representing software that sets forth the preferred iris-angle calculator 42 and ICL calculator 44 for a patient's eye. This allows a physician to accurately fit an ICL for a patient and thereby achieve optimal results for the patient.

Step 48 of FIG. 2 causes camera 14 and digitizer 38 to acquire multiple images, in a rapid fashion, of the illuminated limbal area. It is preferred that the images be acquired as rapidly as possible to minimize the effects of system 10 and eye 12 movement, therefore allowing for the most accurate measurements.

Step 50 then causes computer 18 to analyze the image scene. This analysis includes several steps including the location of the direct slit image, the limbal illumination ring, the fixation target, and a pupil boundary. The location of these portions of each image are preferably done to the nearest pixel accuracy. This will allow a limbal diameter to be measured to accuracy within 0.1 mm. The next portion of Step [50] includes precisely detecting, preferably to sub-pixel accuracy, the edges of the direct slit image by known techniques. The detected direct slit image is then triangulated into three-dimensional space (3-space) and the outer edges of the limbal-ring are then precisely detected. Here the edge is defined as a mid-threshold point near the maximum gradient in back scattered illumination. And finally Step 50 concludes with preferably precisely locating a centroid of the fixation target 24 that is projected onto the eye as described above.

Step 52 then determines the limbal figure, which is defined as the annular area between the detected edges of Step 50 of the limbal-ring projected onto the best limbal plane. The best limbal plane is determined by known techniques. Imaging and measurements are then preferably registered to a common coordinate system to eliminate instrument and eye movement between the multiple images. The best limbal plane in 3-space is then determined from the triangulated slit measurements of Step 50. Next, the limbal edges are projected onto the best limbal plane. And finally, the different limbal edges are integrated from the different images that have been derived from Step 48 and Step 50.

Step 54 then determines the iris-angle diameter and includes iris-angle calculator 42. Preferably, this iris-angle diameter is calculated by interpolating the iris-angle diameter from the measured limbal ring diameter. The accuracy of the interpolation will increase as anatomical research over different populations is accomplished to empirically determine the relationship between limbal-ring diameter and the iris-angle diameter. For example, a diameter of a typical limbal figure will extend from about 10.4 mm to about 13.2 mm. A limbus diameter then of 11 mm will most likely result in an iris-angle diameter which is about a millimeter larger or in the particular example 12 mm. This falls within the limbal figure defined by its inner and outer edges. It is believed that the iris-angle diameter can be accurate to within 0.1 to 0.2 mms where most of the variance comes from anatomical differences. Direct anatomical measurements can be derived from geometrically accurate B-scans of the anterior segment, using ultrasound or optical technologies (e.g., ultrasound biomicroscopy (UBM), or optical coherence tomography (OCT), as well as other technologies. B-scans are 2-D sections constructed from A-scans. A-scans give scattering amplitude versus depth via echo time (UBM) or interference path length (OCT). To generate geometrically accurate B-scans from the original A-scans, measurement geometry must be taken into account, in addition to the diagnostic wave speed for translating temporal measurements or path length into A-scan depth, and wave refraction (acoustic or optical) occurring a media interfaces.

Step 56 determines an ICL size and includes ICL calculator 44. Preferably, the ICL size is calculated based on the determined iris-angle diameter. The ICL size is then presented to a user on the display 19 connected to system 10.

Figure 3:
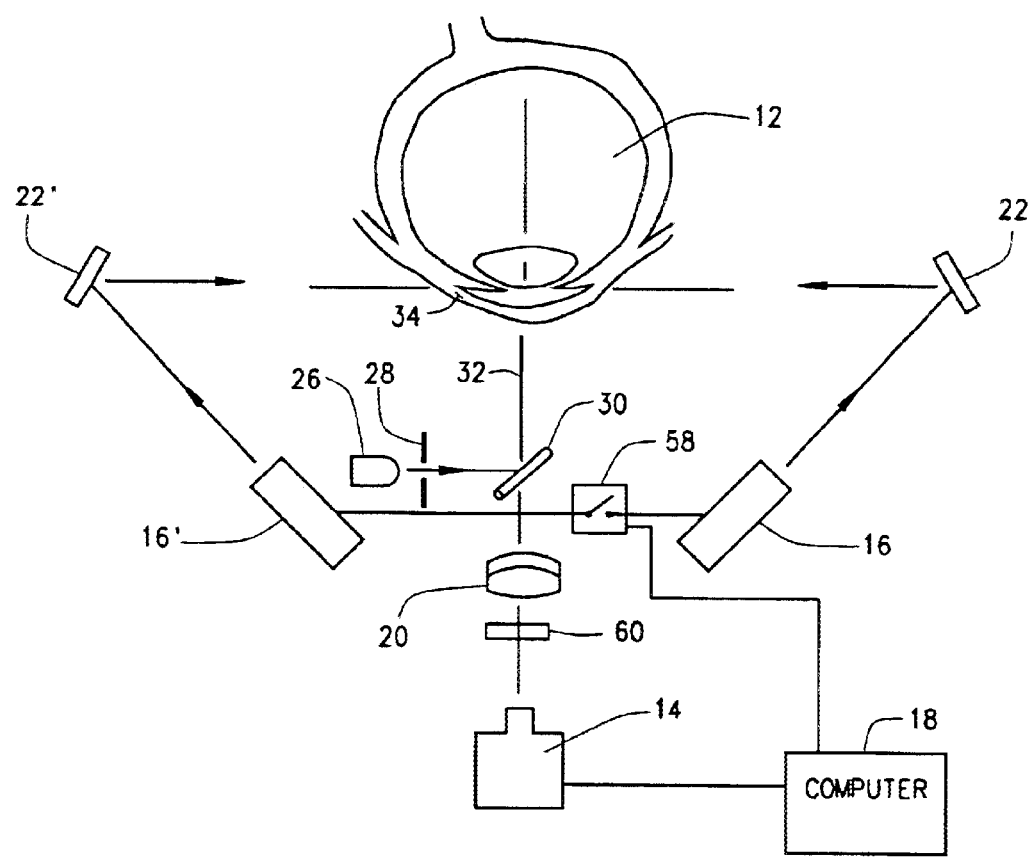
FIG. 3 is a block diagram of an alternate embodiment of a system in accordance with the present invention.

FIG. 3 discloses an alternate embodiment in accordance with the present invention. Specifically, FIG. 3 discloses a system similar to that disclosed above with reference to FIG. 1 except that the embodiment of FIG. 3 includes an additional illumination source 16' and a reflection mirror 22' and also a switching source 58 for sequentially switching the illumination sources 16 and 16' for obtaining the required multiple limbal images. In addition, FIG. 3 shows the use of a light filter 60 for filtering out unwanted light frequencies thereby providing a recorded limbus having an optimal contrasting image.

There has been shown and described a system for measuring the limbal diameter and it will be appreciated that various modifications and variations of the present invention are possible in light of the descriptions set forth without departing from the spirit and scope of the invention. For example, various illumination sources may be used, as well as various image recorders. In addition, system 10 could have a fixed focus and therefore, the entire system 10 is moved relative to the eye 12 until a focused limbus illumination is achieved.

What is claimed is:

1. A system for measuring a diameter of a limbus of an eye comprising:

an image recorder at a known location apart from the eye for recording an illuminated limbus image;

at least a first illumination source at a first known location relative to the image recorder for illuminating the limbus;

a computing device connected to the image recorder for determining the diameter of the limbus from the recorded illuminated limbus;

a second illumination source at a second known location relative to the image recorder for illuminating the limbus;

a switching device connected to the first and second illumination sources for sequentially enabling the first and second illumination sources for allowing the image recorder to record at least one image illuminated by each of the first and second illumination sources; and wherein the computing device combines at least one recorded image illuminated by the first illumination source and at least one recorded image illuminated by the second illumination source for determining the diameter of the limbus.

2. The system of claim 1 further including an output device for displaying the recorded image and diameter of the limbus.

3. The system of claim 1 further including a fixation target associated with the image recorder and for providing the eye with a reference target thereby preventing unwanted eye movement.

4. The system of claim 1 wherein the image recorder is a video camera.

5. The system of claim 1 wherein the illumination source is an infrared source.

6. The system of claim 1 wherein the illumination source is a laser.

7. The system of claim 6 wherein die laser is a slit source.

8. The system of claim 7 wherein the laser is red.

9. The system of claim 1 wherein the computing device further includes an iris-angle diameter calculator for calculating a diameter of an iris-angle of the eye from the determined limbus diameter.

10. The system of claim 1 wherein the computing device further includes an lens calculator for calculating a proper size for the eye from the determined limbus diameter.

11. The system of claim 1 wherein the system has a fixed focus and therefore the entire system is moved relative to the eye until a focused limbus illumination is achieved.

12. The system of claim 1 wherein the image recorder is located along an optical axis of the eye.

13. The system of claim 1 wherein the image recorder includes a light filter for filtering out unwanted light frequencies thereby providing a recorded limbus having an optimal contrasting image.

14. The system of claim 1 wherein the computing device determines the limbus diameter using triangulation.

15. The system of claim 1 wherein the illumination source is placed at an angle from about 25° to about 90° from the image recorder.

16. An eye measurement system comprising:

a camera for recording an illuminated image of a limbus of an eye wherein the camera is to be placed at a known location from the eye;

first and second laser slit lamps at first and second known locations relative to the camera for illuminating the limbus;

a switch connected to the lamps for alternately enabling the first and second lamps for allowing the camera to record an image of the limbus illuminated by each of the first and second lamps; and a computer including a frame grabber connected to the camera and switch for digitizing the illuminated limbus images and calculating one or more of a limbus diameter, an iris-angle diameter, and an inter-corneal lens size for the eye being measured.

17. The system of claim 16 further including an output device for displaying the recorded image and one or more of the calculated limbus diameter, iris-angle diameter, and the inter-corneal lens size.

18. The system of claim 16 further including a fixation target associated with the camera and for providing the eye with a reference target thereby preventing unwanted eye movement.

19. The system of claim 16 wherein the system has a fixed focus and therefore the entire system is moved relative to the eye until a focused limbus illumination is achieved.

20. The system of claim 16 wherein the image recorder is located along an optical axis of the eye.

21. The system of claim 16 wherein the image recorder includes a light filter for filtering out unwanted light frequencies thereby providing a recorded limbus having an optimal contrasting image.

22. The system of claim 16 wherein the system determines the limbus diameter using triangulation.

23. The system of claim 16 wherein the laser slit lamps are placed at an angle from about 25° to about 90° from the camera.

* * * * *